US006839579B1

United States Patent
Chin

(10) Patent No.: US 6,839,579 B1
(45) Date of Patent: Jan. 4, 2005

(54) TEMPERATURE INDICATING OXIMETRY SENSOR

(75) Inventor: Rodney Chin, Oakland, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 167 days.

(21) Appl. No.: 10/053,500

(22) Filed: Nov. 2, 2001

(51) Int. Cl.[7] ............................................... A61B 5/00
(52) U.S. Cl. ....................................... 600/323; 600/334
(58) Field of Search .............................. 600/309–310, 600/322–326, 334

(56) References Cited

U.S. PATENT DOCUMENTS

| | | | |
|---|---|---|---|
| 3,951,133 A | * 4/1976 | Reese | .......................... 600/549 |
| 4,302,971 A | 12/1981 | Luk | |
| 4,859,360 A | * 8/1989 | Suzuki et al. | ............ 252/299.7 |
| 4,926,867 A | 5/1990 | Kanda et al. | |
| 5,007,423 A | * 4/1991 | Branstetter et al. | ......... 600/334 |
| 5,304,003 A | 4/1994 | Winninger | |
| 5,476,489 A | 12/1995 | Koewler | |
| 5,575,284 A | * 11/1996 | Athan et al. | ................. 600/323 |
| 5,673,692 A | 10/1997 | Schulze et al. | |
| 5,686,153 A | 11/1997 | Heynderickx et al. | |
| 5,964,701 A | * 10/1999 | Asada et al. | ................. 600/300 |
| 6,083,156 A | 7/2000 | Lisiecki | |
| 6,115,621 A | * 9/2000 | Chin | .......................... 600/323 |
| 6,454,707 B1 | * 9/2002 | Casscells et al. | ........... 600/300 |

\* cited by examiner

*Primary Examiner*—Eric F. Winakur
*Assistant Examiner*—Matthew Kremer
(74) *Attorney, Agent, or Firm*—Townsend and Townsend and Crew LLP

(57) ABSTRACT

A pulse oximetry sensor having a temperature indicator and a method of operating such a sensor to visually indicate to an operator the temperature of the sensor and hence a measure of the temperature of the tissue location to which the sensor is attached. In one embodiment, the temperature indicator is a color changing liquid crystal temperature monitor. The liquid crystal temperature monitor includes a number of segments, each of which is activateable within a predetermined temperature range to be monitored. In other embodiments of the present invention, the oximetry sensor includes an active regulated heating element to enhance blood perfusion within the tissue location being monitored. In either embodiment, the temperature indicator provides the operator with an effective way of monitoring the temperature of the sensor and the adjacent tissue location. In case of a heated sensor, the temperature indicator informs the operator that the warming function of the sensor is functioning correctly. In case of a nonheated sensor, the temperature indicator informs the operator regarding a measure of the degree of perfusion.

28 Claims, 1 Drawing Sheet

TEMPERATURE INDICATING OXIMETRY SENSOR

BACKGROUND OF THE INVENTION

The present invention relates to oximeter sensors and, in particular, oximeter sensors with a heating element to improve perfusion.

Pulse oximetry is typically used to measure various blood characteristics including, but not limited to, the blood-oxygen saturation of hemoglobin in arterial blood, and the rate of blood pulsations corresponding to the heart rate of a patient. Measurement of these characteristics has been accomplished by use of a noninvasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted or reflected light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Heaters have been used in sensors to improve the perfusion, or amount of blood, adjacent the sensor. This will improve the measurement since the light will encounter a larger volume of blood, giving a better signal-to-noise ratio for the oximeter reading.

Because the normal human body core temperature is approximately 37° C., and burning of tissue could take place for temperatures above approximately 42–43° C., a tight range of control of the heating element is required. Although heating devices can be designed to automatically control the temperature of the sensor and hence the patient's tissue, there exists a need for a simple, low cost and effective way of assuring the operator of such a device that the warming feature of the sensor is correctly functioning. Moreover, in cases of nonheated sensors, a need also exists for a simple, low cost and effective way of indicating a degree of tissue perfusion by showing the temperature of a particular tissue location in contact with the sensor.

BRIEF SUMMARY OF THE INVENTION

The embodiments of the present invention provide for a pulse oximetry sensor having a temperature indicator to visually indicate to an operator the temperature of the sensor and hence a measure of the temperature of the tissue location to which the sensor is attached. In one embodiment, the temperature indicator is a color changing liquid crystal temperature monitor. The liquid crystal temperature monitor includes a number of segments, each of which is activateable within a predetermined temperature range to be monitored. In other embodiments of the present invention, the oximetry sensor includes a heating element to enhance blood perfusion within the tissue location being monitored. In either embodiment, the temperature indicator provides the operator with an effective way of monitoring the temperature of the sensor and the adjacent tissue location. In case of a heated sensor, the temperature indicator informs the operator that the warming function of the sensor is functioning correctly. In case of a nonheated sensor, the temperature indicator informs the operator regarding a measure of the degree of perfusion.

For a further understanding of the nature and advantages of the invention, reference should be made to the following description taken in conjunction with the accompanying drawings.

DETAILED DESCRIPTION OF THE INVENTION

Figure 1:
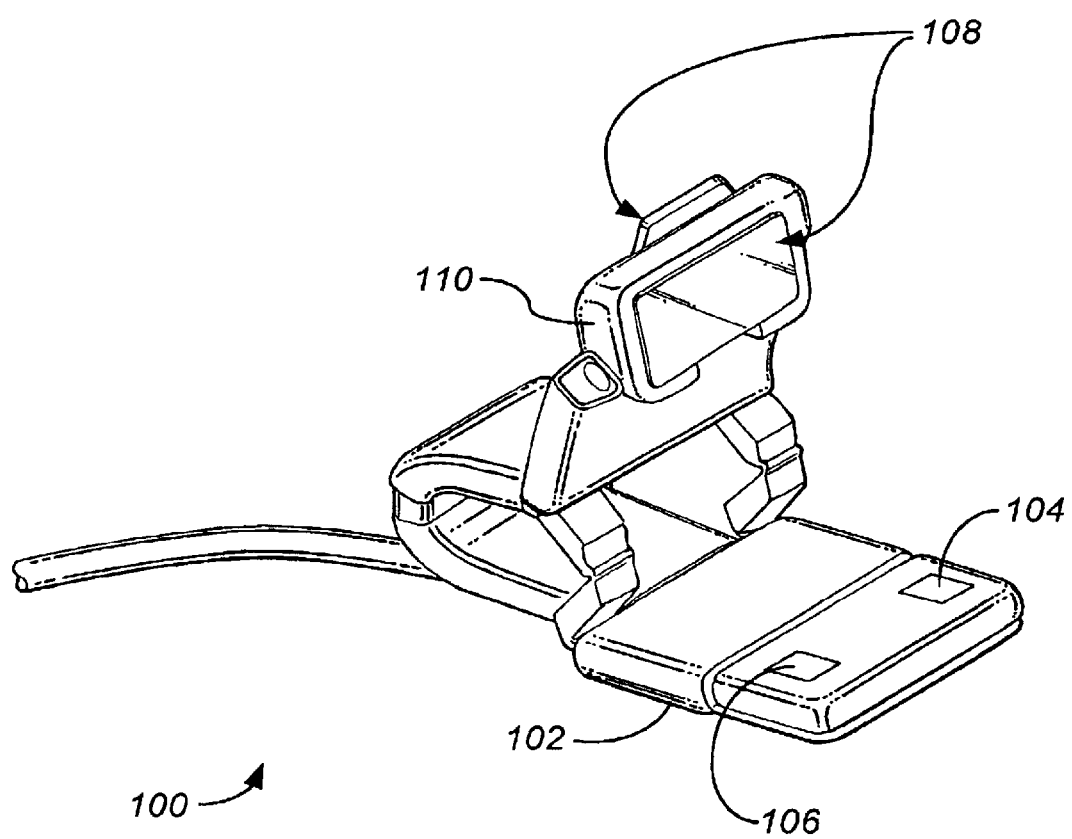
FIG. 1 is a drawing of an oximetry sensor having a temperature indicator.

FIG. 1. shows an oximetry sensor 100 which has been configured to include a temperature indicator 108. In one embodiment, the temperature indicator is a color changing temperature indicator. Alternate embodiments of the temperature indicator are temperature indicators that show temperature numbers in either black, white or gray on a scaled indicator, with the numbers being at different locations on a scale, and numbers being activated to a color other than the indicator's background color depending on the temperature of the surface being sensed. In certain embodiments, the sensor 100 includes a warming device 110 and is similar to a sensor described in a pending patent application titled "Single Device for Both Heating and Temperature Measurement in an Oximeter Sensor;" application Ser. No. 09/447,449 assigned to the assignee herein, the entire disclosure of which is hereby incorporated by reference. Additionally, certain embodiments of the sensor of the present invention use emitters and a detector which are offset from each other, as described in another pending patent application titled "Oximeter Sensor with Offset Emitters and Detector and Heating Device;" application Ser. No. 09/483,098 assigned to the assignee herein, the entire disclosure of which is hereby incorporated by reference. The sensor 100 has a body 102 which is configured to be placed near a patient's body location, such as an ear lobe or a finger. The sensor 100 has a light source 104 connected to the body 102 for providing light to the patient tissue location, and a light collector 106 also connected to the body 102 to collect light that comes from the patient tissue location. In the embodiment shown in FIG. 1, the sensor 100 uses a warming device 110 to increase the local temperature of the tissue to enhance blood perfusion to provide for improved pulse oximetry readings.

As described above, in one embodiment, the temperature indicator 108 is a color-changing temperature indicator. The temperature indicator may consist of a series of different segments of color changing material, each changing color at a different temperature. One embodiment will use a color indicator having two segments, where one segment is blue and the other is red, and where red would indicate a temperature of a warm sensor and blue would indicate a temperature of a nonwarmed sensor. In an alternate embodiment, the temperature indicator will have three colored segments, consisting of a red segment, a yellow segment and a blue segment. In this embodiment, the red segment would indicate a temperature of warm sensor, the blue a temperature of a nonwarm sensor and the yellow an intermediate temperature. In either embodiment, the color indicators are chosen to indicate a temperature range between 37 and 42° C. The red colored segment then corresponds to the maximum temperature of 42° C., the blue segment to the 37° C. and the yellow to a range of temperatures between the maximum of 42° C. and minimum of 37° C. The color-changing temperature indicator may be a liquid crystal-type material or other suitable material. Besides using color to indicate a temperature value, alternate temperature indicators may be used. These alternate temperature indicators may have temperature numbers superimposed on a background, and once a particular temperature is sensed, the number corresponding to that temperature changes to a color which is different from the background (e.g., white active numbers on a black background). Other temperature indicators have a brightly colored line which moves on a temperature scale in response to the sensed temperature.

As shown on FIG. 1, the temperature indicator 108 may be attached to either an external or an internal surface of a pulse oximetry sensor. The embodiments where the temperature indicator is attached to the external surface of the oximeter allow for a clinician to visually monitor the temperature of the sensor while the sensor is in use—such as for pulse oximetry readings. On the other hand, embodiments attaching the temperature indicator to an internal surface allow a clinician to monitor the temperature of the sensor before it is placed in contact with a patient.

In particular, in the embodiments using an external temperature indicator, a material having a high thermal conductivity, such as copper, is placed between the inner surface of the sensor which is in contact with the skin and the outer surface of the sensor, which is in contact with the temperature indicator, to insure that there is not a large (e.g., greater than 2° C.) temperature difference between the temperature indicator and the sensor, in order to provide a reliable indication of temperature. Alternately, the temperature indicator may be calibrated to account for a temperature difference between the actual location where temperature is sensed versus the external surface of the sensor, where the indicator is attached. For example, in a case where there is a 2° C. temperature difference between the inner and outer surface of the sensor, the externally placed temperature indicator would be calibrated to indicate red at 40° C., or the temperature value of 40° C., recognizing that the inner surface is at 42° C.

On the other hand, embodiments having the temperature indicator attached to the inner surface of the oximeter sensor provide an additional level of assurance to the clinician that the oximeter sensor is at a temperature appropriately low enough to be placed next to a patient's skin. This inner-surface attached embodiment is particularly more relevant in the case of a warmed sensor, where the clinician can be assured that the sensor's warming mechanism is functioning properly and that the sensor is at the right temperature before it is placed in contact with the patient's skin. Moreover, the inner-surface attached embodiments provide a more reliable temperature of the surface of the sensor which is in contact with the patient's skin, since the temperature indicator shows the temperature of the surface which is nearest to the patient's skin (i.e., the internal surface). Other alternate embodiments would have temperature indicators attached both to the internal surface and the external surface of the oximeter sensor. Using such a dual temperature indicating sensor, a clinician would look at the inner temperature indicator before placing the sensor in contact with the patient, for reasons explained above. After having attached the sensor to the patient, the clinician would want to continue to monitor the temperature of the sensor by looking at the externally attached sensor, to ascertain that the sensor is at a proper temperature without having to look at the internally attached sensor which would require the removal of the sensor from the patient.

Certain specific embodiments of the present invention use temperature indicators that produce a reversible change in color. Such embodiments will allow for an ongoing monitoring of the sensor's temperature. Other embodiments use temperature indicators that produce an irreversible color change. The irreversible type temperature indicator may be used by itself or in addition to a reversible type temperature indicator. Moreover, the irreversible temperature indicator is of a type which begins to sense a temperature once it is activated by the clinician. The feature of activating an irreversible temperature indicator will ensure that the indicated temperature is one that was sensed during a patient monitoring session and not one that was sensed while the sensor was in storage. The advantage of using an irreversible type temperature indictor is that a measure of the maximum and/or minimum attained temperature during patient monitoring is provided, which outlasts the patient monitoring duration. In this manner, the clinician has the option of looking at a sensor, after not having seen the patient for hours, and see the maximum or minimum temperature attained is the past, even though the current temperature may be different from the previously achieved maximum or minimum temperature.

Another embodiment of the present invention is directed towards the use of a temperature indicator on a sensor that does not employ a warming device. The temperature indicator used in this manner on a conventional (i.e., nonheated) sensors is used to indicate the temperature of the sensor and its adjacent tissue location to suggest a degree of blood perfusion. A temperature indicator on a nonheated sensor allows for a determination of the level of perfusion in the tissue location being sensed, and thus if it is determined that the location suffers from poor perfusion (e.g., low temperature), the clinician is able to adjust the attachment site until a better-perfused location is found.

Although the temperature indicator can be used with both the heated or nonheated oximeter sensors, for a heated sensor it is preferred to have the temperature indicator be placed on the sensor on an opposite side from the heater. This preferred placement will allow for the temperature indicator to provide a better indication of the bulk-average temperature of the sensor.

As will be understood by those of skill in the art, the present invention may be embodied in other specific forms without departing from the essential characteristics thereof. For example, the temperature indicator could be placed at any location on the sensor; the temperature indicator may be either a liquid crystal temperature monitor, a color-changing temperature indicator or any other suitable temperature indicator. Accordingly, the foregoing description is intended to be illustrative, but not limiting, of the scope of the invention which is set forth in the following claims.

What is claimed is:

1. An oximeter sensor comprising:
   a body configured to be placed near a patient;
   a light source connected to said body to provide light to said patient;
   a light collector connected to said body to collect light from said patient; and
   a passive non-electronic temperature indicator mounted on said body to provide a visual indication of the temperature of said sensor, said temperature indicator not being in electrical communication with said sensor or with a processor of said sensor.

2. The sensor of claim 1 further comprising an active heating element connected to said body.

3. The sensor of claim 1 wherein said body has an external surface, and wherein said temperature indicator is mounted on said external surface such that said temperature indicator is visible to a clinician when said sensor is in use.

4. The sensor of claim 1 wherein said body has an internal surface, and wherein said temperature indicator is mounted on said internal surface such that said temperature indicator is visible to a clinician before said sensor is attached to a patient.

5. The sensor of claim 1 wherein said temperature indicator comprises a color-changing temperature indicator.

6. The sensor of claim 1 wherein said temperature indicator comprises a liquid crystal temperature monitor.

7. The sensor of claim 1 wherein said temperature indicator comprises a number of segments of a color-changing temperature indicators, each activateable within a predetermined temperature range so as to provide a color-changing visual indication of the temperature of said sensor.

8. The sensor of claim 1 wherein said temperature indicator comprises a number of deposits of liquid crystals, each activateable within a predetermined temperature range so as to provide a color-changing visual indication of the temperature of said sensor.

9. The sensor of claim 1 wherein said temperature indicator produces a reversible color change.

10. The sensor of claim 1 wherein said temperature indicator produces an irreversible color change.

11. The sensor of claim 1 wherein said sensor is configured to be applied to one of an ear lobe and a pinna.

12. An oximeter sensor comprising:
   a body configured to be placed near a patient;
   a light source connected to said body to provide light to said patient;
   a light collector connected to said body to collect light from said patient; and
   a passive non-electronic color-changing temperature indicator mounted on said body to provide a visual indication of the temperature of said sensor, wherein said color-changing temperature indicator comprises a liquid crystal temperature monitor, said temperature indicator not being in electrical communication with said sensor or with a processor of said sensor.

13. The sensor of claim 12 further comprising an active heating element connected to said body.

14. The sensor of claim 12 wherein said color-changing temperature indicator produces a reversible color change.

15. The sensor of claim 12 wherein said sensor is configured to be applied to one of an ear lobe and a pinna.

16. A method for operating an oximeter sensor, comprising:
   activating a light source to provide light to a patient;
   detecting light from said patient; and
   providing a visual indication of the temperature of said sensor using a passive non-electronic temperature indicator that is not in electrical communication with said sensor or with a processor of said sensor.

17. The method of claim 16 further comprising:
   providing power to an active heating device;
   heating said patient using said heating device;
   determining the temperature of said sensor; and
   modifying the amount of power provided to said device in accordance with said temperature.

18. The method of claim 16 wherein said visual indication is provided by a temperature indicator placed on said sensor.

19. The method of claim 16 wherein said visual indication is provided by a liquid crystal temperature monitor.

20. The method of claim 16 wherein said visual indication is provided by a number of segments of a color-changing temperature indicators, where each of said segments are activateable within a predetermined temperature range.

21. The method of claim 16 wherein said visual indication is provided by a number of deposits of liquid crystals, wherein each of said number of deposits is activateable within a predetermined temperature range.

22. The method of claim 16 wherein said visual indication comprises a reversible color change.

23. The method of claim 16 wherein said visual indication comprises an irreversible color change.

24. A method for operating an oximeter sensor, comprising:
   activating a light source to provide light to a patient;
   detecting light from said patient; and
   providing a visual indication of the temperature of said sensor by a using a passive non-electronic temperature indicator, wherein said temperature indicator comprises a liquid crystal temperature monitor that is not in electrical communication with said sensor or with a processor of said sensor.

25. The method of claim 24 further comprising:
   providing power to an active heating device;
   heating said patient using said heating device;
   determining the temperature of said sensor; and
   modifying the amount of power provided to said device in accordance with said temperature.

26. The method of claim 24 wherein said visual indication is provided by a liquid crystal temperature monitor.

27. The method of claim 24 wherein said visual indication is a reversible color change.

28. The method of claim 24 wherein said visual indication is an irreversible color change.

* * * * *

UNITED STATES PATENT AND TRADEMARK OFFICE
CERTIFICATE OF CORRECTION

PATENT NO. : 6,839,579 B1  
DATED : January 4, 2005  
INVENTOR(S) : Rodney Chin

It is certified that error appears in the above-identified patent and that said Letters Patent is hereby corrected as shown below:

<u>Title page,</u>  
Item [*] Notice, should read:  
-- Subject to any disclaimer, ther term of this patent is extended or adjusted under 35 U.S.C. 154(b) by 182 days. --.

Signed and Sealed this

Eleventh Day of April, 2006

JON W. DUDAS  
*Director of the United States Patent and Trademark Office*